United States Patent

Rutsch et al.

[11] Patent Number: 5,218,009
[45] Date of Patent: Jun. 8, 1993

[54] MONO- AND DI-ACYLPHOSPHINE OXIDES

[75] Inventors: Werner Rutsch; Kurt Dietliker, both of Fribourg; Roger G. Hall, Aesch, all of Switzerland

[73] Assignee: Ciba-Geigy Corporation, Ardsley, N.Y.

[21] Appl. No.: 751,048

[22] Filed: Aug. 28, 1991

Related U.S. Application Data

[63] Continuation-in-part of Ser. No. 559,462, Jul. 30, 1990, abandoned.

[30] Foreign Application Priority Data

Aug. 4, 1989 [CH] Switzerland ............... 2897/89

[51] Int. Cl.$^5$ ............... C08F 2/50; C07F 9/02
[52] U.S. Cl. ............... 522/16; 568/15; 522/81; 522/100; 522/104; 522/121; 522/18; 522/64
[58] Field of Search ............ 522/64, 81, 100, 104, 522/121, 16, 18; 568/15

[56] References Cited

U.S. PATENT DOCUMENTS

| | | | |
|---|---|---|---|
| 3,957,512 | 5/1976 | Kleeberg et al. | 96/35.1 |
| 4,292,152 | 9/1981 | Lechtken et al. | 204/159.15 |
| 4,298,738 | 11/1981 | Lechtken et al. | 546/22 |
| 4,324,744 | 4/1982 | Lechtken et al. | 260/932 |
| 4,385,109 | 5/1983 | Lechtken et al. | 430/306 |
| 4,447,520 | 5/1984 | Henne et al. | 430/281 |
| 4,710,523 | 12/1987 | Lechtken et al. | 522/14 |
| 4,737,593 | 4/1988 | Ellrich et al. | 568/15 |
| 4,792,632 | 12/1988 | Ellrich et al. | 568/15 |
| 5,008,426 | 4/1991 | Kleiner et al. | 558/82 |

FOREIGN PATENT DOCUMENTS 3245297 6/1984 Fed. Rep. of Germany.

OTHER PUBLICATIONS

Houben-Weyl, Methoden d. Org. Chem. XII/1, 324–327 (1963).
Houben-Weyl, Methoden d. Org. Chem. XII/1, 60–63 (1963).
Houben-Weyl, Methoden d. Org. Chem. XII/1, 208–210 (1963).
Chem. Abst. 70, 11752+ (1969).
T. Sumiyoshi et al., Makromol. Chem., 186, 1811 (1985).

Primary Examiner—Marion E. McCamish
Assistant Examiner—Susan Berman
Attorney, Agent, or Firm—Luther A. R. Hall

[57] ABSTRACT

Compounds of the formula I

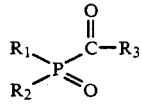

in which at least one of the radicals $R_1$, $R_2$ and $R_3$ is a substituted alkyl radical or cycloalkyl radical, or $R_1$ and $R_2$ together with the phosphorus atom form a monocyclic or tricyclic ring, are effective photoinitiators for the photopolymerization of ethylenically unsaturated compounds.

20 Claims, No Drawings

MONO- AND DI-ACYLPHOSPHINE OXIDES

This is a continuation-in-part of application Ser. No. 559,462 filed Jul. 30, 1990, now abandoned The invention relates to special mono- and di-acylphosphine oxides and to their use as photoinitiators for the photopolymerization of ethylenically unsaturated compounds.

Monoacylphosphine oxides are known as photoinitiators from EP-A-7,508. Bisacylphosphine oxides and their use as photoinitiators are known from EP-A-184,095. Novel mono- and bis-acylphosphine oxides have now been found which differ from the known compounds by the presence of certain substituents. These are compounds of the formula I

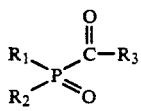

in which $R_1$ is $C_1$–$C_{18}$alkyl, $C_2$–$C_{18}$alkenyl, $C_1$–$C_8$alkyl which is monosubstituted or polysubstituted by phenyl, ($C_1$–$C_{12}$alkyl)-phenyl, halogenophenyl, ($C_1$–$C_{12}$alkoxy)-phenyl, cyano, $C_2$–$C_5$alkoxycarbonyl, $C_1$–$C_{12}$alkoxy or/and halogen, $C_5$–$C_8$cycloalkyl, $C_6$–$C_{12}$aryl, which is unsubstituted or mono- or poly-substituted by halogen, $C_1$–$C_{12}$alkyl or/and $C_1$–$C_{12}$alkoxy, a 5-membered or 6-heterocyclic monovalent radical which contains one or more O, S or/and N atoms and which may contain a fused benzo radical or/and which is unsubstituted or substituted by $C_1$–$C_4$alkyl, $C_1$–$C_4$alkoxy or/and halogen, or is a radical of the formula

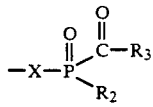

in which X is phenylene, xylylene, cyclohexylene or $C_1$–$C_6$alkylene which may be unsubstituted or monosubstituted or polysubstituteds by halogen, $C_1$–$C_4$alkyl, $C_1$–$C_4$alkoxy or phenyl, $R_2$ is $C_1$–$C_{18}$alkyl, $C_2$–$C_{18}$alkenyl, $C_1$–$C_8$alkyl which is monosubstituted or polysubstituted by phenyl, ($C_1$–$C_{12}$alkyl)-phenyl, halogenophenyl, ($C_1$–$C_{12}$alkoxy)-phenyl, cyano, $C_2$–$C_5$alkoxycarbonyl, $C_1$–$C_{12}$alkoxy or/and halogen, $C_5$–$C_8$cycloalkyl, $C_6$–$C_{12}$aryl which is unsubstituted or mono- or poly-substituted by halogen, $C_1$–$C_{12}$alkyl or/and $C_1$–$C_{12}$alkoxy, a 5-membered or 6-membered heterocyclic monovalent radical which contains one or more O, S or N atoms and which may contain a fused benzo radical or/and is unsubstituted or substituted by $C_1$–$C_4$alkyl, $C_1$–$C_4$alkoxy or/and halogen, or is a radical —CO—$R_3$ or —O$R_4$, or $R_1$ and $R_2$ or $R_1$ and $R_4$ together with the phosphorus atom form a monocyclic or bicyclic or tricyclic ring having 4–15 C atoms, $R_3$ is $C_1$–$C_{18}$alkyl, $C_2$–$C_6$alkenyl, phenylvinyl, $C_1$–$C_8$alkyl which is mono- or poly-substituted by phenyl, $C_2$–$C_5$alkoxycarbonyl, halogen, $C_1$–$C_{12}$alkoxy, phenoxy, $C_1$–$C_{12}$alkylthio or/and phenylthio, $C_5$–$C_{10}$cycloalkyl which is unsubstituted or substituted by $C_1$–$C_{12}$alkyl, phenyl, phenoxy, $C_1$–$C_{12}$alkoxy, $C_2$–$C_5$alkoxycarbonyl, $C_1$–$C_4$alkylthio or/and halogen, $C_6$–$C_{12}$aryl which is unsubstituted or mono- or poly-substituted by $C_1$–$C_{12}$alkyl, $C_1$–$C_{12}$alkoxy, $C_1$–$C_{12}$alkoxyalkyl, $C_1$–$C_4$alkylthio or/and halogen, or a monovalent 5-membered or 6-membered heterocyclic radical containing one or more O, S or N atoms, which radical can be mono- or poly-substituted by halogen, $C_1$–$C_4$alkyl or $C_1$–$C_4$alkoxy, and $R_4$ is $C_1$–$C_{18}$alkyl, phenyl-$C_1$–$C_4$alkyl, $C_5$–$C_8$cycloalkyl or $C_6$–$C_{10}$aryl, with the proviso that at least one of the radicals $R_1$, $R_2$ and $R_3$ is a substituted alkyl radical or that $R_1$ and $R_2$ together with the phosphorus atom form a bicyclic or tricyclic ring, or that $R_3$ is a substituted cycloalkyl radical which, however, cannot contain alkyl radicals as the only substituents.

$C_1$–$C_{18}$Alkyl $R_1$, $R_2$, $R_3$ and $R_4$ can be branched or unbranched alkyl and can, for example, be methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl or octadecyl.

Alkyl $R_3$ is preferably tertiary alkyl, for example tert-butyl, 1,1-dimethylpropyl, 1,1-dimethylbutyl or 1,1,3,3-tetramethylbutyl.

$C_2$–$C_{18}$Alkenyl $R_1$ and $R_2$ can, for example be vinyl, allyl, methallyl, 1,1-dimethylallyl, 2-butenyl, 2-hexenyl, octenyl, undecenyl, dodecenyl or octadecenyl. Furthermore, $C_2$–$C_{18}$alkenyl $R_4$ can also be vinyl.

$C_2$–$C_6$Alkenyl $R_3$ can, for example, be vinyl, propenyl or butenyl.

$C_1$–$C_8$Alkyl $R_1$ and $R_2$, which is monosubstituted or polysubstituted, for example monosubstituted to trisubstituted, especially monosubstituted or disubstituted, can, for example, be benzyl, 1-phenylethyl, 2-phenylethyl, α,α-dimethylbenzyl, benzhydryl, p-tolylmethyl, 1-(p-butylphenyl)-ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di-(methoxycarbonyl)-ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl or trifluoromethyl, preferably benzyl.

$C_1$–$C_8$Alkyl $R_3$, which is mono- or poly-substituted, for example mono- to tri-substituted, especially mono- or di-substituted, can, for example, be benzyl, phenylethyl, α,α-dimethylbenzyl, benzhydryl, 1,1-dichloroethyl, trichloromethyl, trifluoromethyl, 1,1-dimethyl-2-chloroethyl, 2-methoxyisopropyl, 2-ethoxyethyl, butylthiomethyl, 2-dodecylthioethyl or 2-phenylthioethyl.

$C_1$–$C_8$Alkyl $R_4$ which is mono- or poly-substituted, for example mono- to tri-substituted, especially mono- or di-substituted, can, for example, be benzyl, 2-phenylethyl, 3-phenylpropyl, 2-methoxyethyl, 2-butoxyethyl, 2-hexyloxyethyl, 2-isopropoxypropyl, 2-chloroethyl or 2,2,2-trifluoroethyl.

$C_5$–$C_8$Cycloalkyl $R_1$, $R_2$, $R_3$ and $R_4$ can, for example, be cyclopentyl, cyclohexyl or cyclooctyl. $C_5$–$C_{10}$Cycloalkyl $R_3$ which is, for example, mono- to tetra-substituted, can, for example, be methylcyclopentyl, dimethylcyclopentyl, methylcycloyhexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl or dichlorocyclopentyl or a saturated or unsaturated bicyclic system, for example norbornyl or norbornenyl.

$C_6$–$C_{12}$Aryl $R_1$, $R_2$, $R_3$ and $R_4$ can, for example, be phenyl, α-naphthyl, β-naphthyl or 4-diphenylyl, especially phenyl. Substituted $C_6-C_{12}$aryl $R_1$, $R_2$ and $R_3$ can, for example, be chlorophenyl, dichlorophenyl, trichlorophenyl, difluorophenyl, tolyl, ethylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl or ethoxynaphthyl. Furthermore, substituted aryl $R_3$ can also, for example, be methoxyethylphenyl, ethoxymethylphenyl, methylthiophenyl, isopropylthiophenyl or tert-butylthiophenyl. Substituted aryl also is preferably substituted phenyl.

A heterocyclic radical $R_1$, $R_2$ and $R_3$ can, for example, be furyl, thienyl, pyrryl, pyridyl, indolyl, benzoxazolyl, dioxolyl, dioxyl, benzimidazolyl or benzothiazolyl. Preferably, such a heterocyclic radical contains 3–12 C atoms, especially 3–5 C atoms. Substituted heterocyclic radicals (for example mono- to tri-substituted and especially mono- or di-substituted heterocyclic radicals) can, for example, be dimethylpyridyl, methylquinolyl, dimethylpyrryl, methoxyfuryl, dimethoxypyridyl or difluoropyridyl.

$C_1-C_6$Alkylene X can, for example, be methylene, 1,2-ethylene, 2,2-dimethyl-1,3-propylene, trimethylene, tetramethylene, pentamethylene, hexamethylene or phenylmethylene.

A monocyclic ring formed by $R_1$ and $R_2$ together with the P atom is preferably a phosphacyclopentane ring.

A bicyclic ring formed by $R_1$ and $R_2$ together with the P atom is preferably a phosphabicyclohexane or phosphabicyclononane ring.

A tricyclic ring formed by $R_1$ and $R_4$ together with the P atom is preferably a (6H)-dibenzo[c,e][1,2]oxaphosphorine ring.

Those compounds of the formula I are preferred in which $R_1$ is $C_1-C_{12}$alkyl, $C_1-C_4$alkyl which is mono- to tri-substituted by phenyl, ($C_1-C_4$alkyl)-phenyl, chlorophenyl, ($C_1-C_4$alkoxy)-phenyl or/and $C_1-C_4$alkoxy, cyclohexyl, $C_6-C_{10}$aryl which is unsubstituted or mono- to tri-substituted by chlorine, $C_1-C_{12}$alkyl or/and $C_1-C_4$alkoxy, or is a 5-membered or 6-membered heterocyclic monovalent radical which contains one or more O, S or N atoms, $R_2$ is as defined for $R_1$ or a radical —CO—$R_3$ or —OR$_4$, or $R_1$ and $R_2$ or $R_1$ and $R_4$ together with the P atom form a monocyclic or bicyclic radical having 4–8 C atoms, $R_3$ is $C_1-C_8$alkyl, $C_1-C_6$alkyl which is mono- or di-substituted by phenyl, $C_1-C_4$alkoxy, $C_2-C_5$alkoxycarbonyl or/and chlorine, $C_5-C_6$cycloalkyl which is unsubstituted or substituted by phenyl, $C_1-C_4$alkoxy, $C_2-C_5$alkoxycarbonyl or/and chlorine, or $C_6-C_{10}$aryl which is unsubstituted or mono- to tri-substituted by $C_1-C_{12}$alkyl, $C_1-C_4$alkoxy or/and chlorine, and $R_4$ is $C_1-C_8$alkyl, cyclohexyl, benzyl or phenyl, and especially those in which $R_1$ is $C_1-C_8$alkyl, $C_1-C_4$alkyl which is mono- or di-substituted by phenyl, ($C_1-C_4$alkyl)-phenyl or $C_1-C_4$alkoxy, cyclohexyl or phenyl which is unsubstituted or mono- to tri-substituted by $C_1-C_4$alkyl or $C_1-C_4$alkoxy, $R_2$ is as defined for $R_1$ or is a radical —CO—$R_3$ or —OR$_4$, or $R_1$ and $R_2$ or $R_1$ and $R_4$ together with the P atom form a monocyclic or bicyclic ring, $R_3$ is $C_1-C_6$alkyl which is unsubstituted or substituted by phenyl, chlorine or/and $C_1-C_4$alkoxy, $C_5-C_6$cycloalkyl which is unsubstituted or substituted by phenyl, $C_1-C_4$alkoxy, $C_2-C_5$alkoxycarbonyl or/and chlorine, or phenyl which is unsubstituted or mono- to tri-substituted by $C_1-C_4$alkyl, $C_1-C_4$alkoxy or/and chlorine, and $R_4$ is $C_1-C_4$alkyl, cyclohexyl or phenyl.

Preferably, $R_1$ is a substituted alkyl radical as defined above, especially $C_1-C_4$alkyl which is mono- to di-substituted by phenyl, ($C_1-C_4$alkyl)-phenyl or $C_1-C_4$alkoxy and with particular preference is benzyl.

$R_3$ is especially a phenyl radical which is substituted in both ortho-positions by $C_1-C_4$alkyl, $C_1-C_4$alkoxy or chlorine.

Moreover, bicyclic compounds of the formula II or III

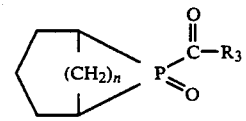

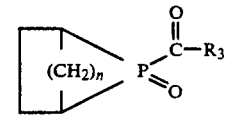

are preferred, in which n is 1–8 and $R_3$ is as defined above, in particular those compounds of the formula II or III in which n is 1–8, especially 1–4, and $R_3$ is $C_1-C_4$alkyl substituted by phenyl, $C_6-C_{10}$aryl or phenyl which is mono- to tri-substituted by $C_1-C_{12}$alkyl, $C_1-C_4$alkoxy or chlorine.

Examples of individual compounds of the formula I are:
dibenzyl-(2,4,6-trimethylbenzoyl)-phosphine oxide
bis(2-phenylethyl)-(2,6-dichlorobenzoyl)-phosphine oxide
bis(2-phenylpropyl)-(2,6-dimethoxybenzoyl)-phosphine oxide
bis(2-phenylpropyl)-(2,4,6-trimethylbenzoyl)-phosphine oxide
bis(2-cyanoethyl)-(2,4,6-trimethylbenzoyl)-phosphine oxide
methyl 2-phenylpropyl-(2,4,6-trimethylbenzoyl)-phosphinate
6-[bis(chloromethyl)propionyl]-(6H)-dibenz[c,e][1,2]oxaphosphorine 6-oxide
methyl phenyl-(2,2-dimethyl-3-phenylpropionyl)-phosphinate
diphenyl-(2,2-dimethyl-3-phenylpropionyl)-phosphine oxide
diphenyl-2,6-dimethoxycyclohexanoylphosphine oxide
dibutyl-(2-methyl-2-phenylbutyryl)-phosphine oxide
butyl-1,1-diethoxyethyl-2,4,6-trimethylbenzoyl-phosphine oxide
bis(cyclohexyl)-(2-methyl-2-phenylthiopropionyl)-phosphine oxide
diphenyl-(2-octyloxy-2-phenylpropionyl)-phosphine oxide
1-(2,6-dimethylbenzoyl)-phospholan 1-oxide
6-(2,6-dichlorobenzoyl)-6-phosphabicyclo[2.1.1]hexane 6-oxide
9-(2,6-dichlorobenzoyl)-9-phosphabicyclo[3.3.1]nonane 9-oxide
9-(2,4,6-trimethylbenzoyl)-9-phosphabicyclo[4.2.1]nonane 9-oxide
bis(2,6-dichlorobenzoyl)-2-phenylpropylphosphine oxide
bis(2,6-dimethoxybenzoyl)-benzylphosphine oxide
bis(2,6-dimethoxybenzoyl)-2-phenylpropylphosphine oxide bis(2,6-dimethoxybenzoyl)-2-phenylethylphosphine oxide
bis(2,6-dichlorobenzoyl)-benzylphosphine oxide
bis(2,6-dichlorobenzoyl)-2-phenylethylphosphine oxide
bis(2,4,6-trimethylbenzoyl)-benzylphosphine oxide
bis(2,4,6-trimethylbenzoyl)-2-phenylpropylphosphine oxide
bis(2,4,6-trimethylbenzoyl)-2-phenylethylphosphine oxide
bis(2,4,6-trimethylbenzoyl)-2-cyanoethylphosphine oxide
bis(2,6-dichlorobenzoyl)-2-cyanoethylphosphine oxide
bis(2,6-dimethoxybenzoyl)-2-cyanoethylphosphine oxide
bis(2-methylthiobenzoyl)-2-phenylpropylphosphine oxide
bis(2-methyl-1-naphthoyl)-2-phenylpropylphosphine oxide
bis(2-methyl-2-phenylpropionyl)-cyclohexylphosphine oxide
bis(2-methyl-2-phenylbutyryl)-phenylphosphine oxide
bis(2,2-dimethyl-4-phenylbutyryl)-phenylphosphine oxide
bis(2-methoxy-2-phenylbutyryl)-4-propylphenylphosphine oxide
bis(2-methylthio-2-phenylbutyryl)-cyclohexylphosphine oxide
bis(2-methyl-2-phenylthiopropionyl)-2-phenylpropylphosphine oxide
bis(2-methyl-2-phenylbutyryl)-2-phenylpropylphosphine oxide
bis(2-methyl-2-phenylbutyryl)-2-cyclohexylphosphine oxide
(2,6-dichlorobenzoyl)-(1,3-dioxolan-2-yl)-phenylphosphine oxide
diphenyl-(3-phenyl-bicyclo[2.2.1]hept-5-en-2-ylcarbonyl)-phosphine oxide
diphenyl(2-methyl-3-phenyl-bicyclo[2.2.1]heptan-2-ylcarbonyl)-phosphine oxide
2,4,6-trimethylbenzoyl-benzyl-butylphosphine oxide
2,6-dichlorobenzoyl-benzyl-butylphosphine oxide
2,6-dimethoxybenzoyl-benzyl-butylphosphine oxide
2,6-dimethoxybenzoyl-benzyl-octylphosphine oxide
2,6-dichlorobenzoyl-benzyl-octylphosphine oxide
2,4,6-trimethylbenzoyl-benzyl-octylphosphine oxide
2,4,6-trimethylbenzoyl-benzyl-methylphosphine oxide
2,4,6-trimethylbenzoyl-benzyl-cyclohexylphosphine oxide
2,6-dichlorobenzoyl-benzyl-cyclohexylphosphine oxide
2,6-dimethoxybenzoyl-benzyl-cyclohexylphosphine oxide The compounds of the formula I, in which $R_2$ is a radical —$OR_4$, can be prepared by an Arbusow-Michaelis reaction of the corresponding phosphonite IV with a carboxylic acid chloride V according to the equation:

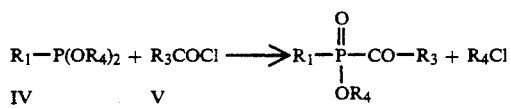

$$R_1-P(OR_4)_2 + R_3COCl \longrightarrow R_1-\overset{\overset{O}{\|}}{\underset{OR_4}{P}}-CO-R_3 + R_4Cl$$

IV      V

The reaction can take place with or without a solvent. If the components IV and V are liquid, it is preferable to work without a solvent. Suitable solvents are especially hydrocarbons such as alkanes and alkane mixtures, benzene, toluene or xylene. The reaction is preferably carried out at 20°–120° C. The $R_4Cl$ being formed is preferably distilled off continuously during the reaction. If a solvent is used, this is dissolved off at the end of the reaction. The crude reaction product can be purified, for example, by distillation, crystallization or chromatography.

The phosphonites IV can be prepared in a known manner by reacting a dichlorophosphine $R_1$—$PCl_2$ with at least 2 mol of $R_4OH$ in the presence of an HCl acceptor (in this connection, see Houben-Weyl, Methoden d. Org. Chemie [Methods of Organic Chemistry] XII/1, 324–327 (1963), G. Thieme-Verlag, Stuttgart).

The compounds of the formula I in which $R_2$ is a radical —$COR_3$ can be prepared by double acylation of a primary phosphine VI with at least 2 equivalents of an acid chloride V in the presence of at least 2 equivalents of a base and subsequent oxidation of the resulting diacylphosphine VII to the phosphine oxide according to the equation:

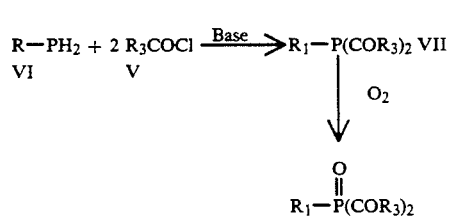

Examples of suitable bases are tertiary amines, alkali metals, lithium diisopropylamide, alkali metal alcoholates or alkali metal hydrides. The first reaction stage preferably takes place in solution. Suitable solvents are especially hydrocarbons, for example alkanes, benzene, toluene or xylene. After the resulting chloride of the base has been separated off, the phosphine VII can be isolated by evaporation, or the second reaction stage is carried out with the solution of the crude product, without isolation of VII. Oxidizing agents suitable for the second stage are especially hydrogen peroxide and organic peroxy compounds, for example peractic acid.

The primary phosphines VI used as the starting material are known compounds or can be prepared analogously to known compounds (in this connection, see Houben-Weyl, Methoden der Org. Chemie [Methods of Organic Chemistry] XII/1, 60–63 (1963), G. Thieme-Verlag, Stuttgart).

The compounds of the formula I in which $R_2$ is neither a radical —$OR_4$ nor a radical —$COR_3$ can be prepared by acylation of secondary phosphines VIII and subsequent oxidation according to the equation:

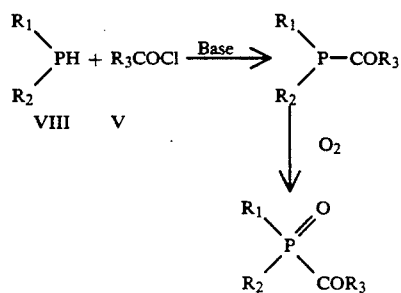

The same comments as above apply to these reactions. The starting phosphines VIII can be otained by known methods, for example by reduction of monochlorophosphines $(R_1)(R_2)PCl$ by means of $LiAlH_4$ (in this connection, see Houben-Weyl, Methoden der Org. Chemie [Methods of Organic Chemistry]XII/1, 60-63 (1963), G. Thieme-Verlag, Stuttgart).

An alternative possibility for the preparation is the Arbusow-Michaelis reaction of phosphinites IX with V according to the equation:

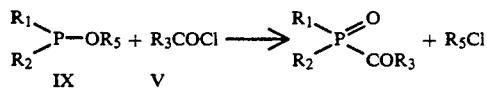

in which $R_5$ is an alkyl radical.

The starting materials IX can be prepared by known methods, for example by alcoholysis of monochlorophosphines $(R_1)(R_2)PCl$ with $R_5OH$ in the presence of bases (in this connection, see Houben-Weyl, Methoden der Org. Chemie [Methods of Organic Chemistry]XII/1, 208-210, 1963), G. Thieme-Verlag, Stuttgart).

According to the invention, the compounds of the formula I can be used as photoinitiators for the photopolymerization of ethylenically unsaturated compounds or of mixtures containing such compounds. The unsaturated compounds can contain one or more olefinic double bonds. They can be low-molecular (monomeric) or higher-molecular (oligomeric). Examples of monomers having one double bond are alkyl or hydroxyalkyl acrylates or methacrylates, such as methyl, ethyl, butyl, 2-ethylhexyl or 2-hydroxyethyl acrylate, isobornyl acrylate and methyl or ethyl methacrylate. Further examples thereof are acrylonitrile, acrylamide, methacrylamide, N-substituted (meth)acrylamides, vinyl esters such as vinyl acetate, vinyl ethers such as isobutyl vinyl ether, styrene, alkylstyrenes and halogenostyrenes, N-vinylpyrrolidone, vinyl chloride or vinylidene chloride.

Examples of monomers having more than one double bond are the diacrylates of ethylene glycol, propylene glycol, neopentyl glycol, hexamethylene glycol or bisphenol A, 4,4'-bis-(2-acryloyloxyethoxy)-diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris-(2-acryloylethyl) isocyanurate.

Examples of higher-molecular (oligomeric) polyunsaturated compounds are acrylated epoxide resins, acrylated polyethers, acrylated polyurethanes or acrylated polyesters. Further examples of unsaturated oligomers are unsaturated polyester resins which are in most cases prepared from maleic acid, phthalic acid and one or more diols, and have molecular weights of about 500 to 3000. Such unsaturated oligomers can also be described as prepolymers.

Frequently, two-component mixtures of a prepolymer with a polyunsaturated monomer or three-component mixtures additionally also containing a monounsaturated monomer are used. In this case, the prepolymer is mainly responsible for the properties of the paint film, and those skilled in the art can influence the properties of the cured film by varying this prepolymer. The polyunsaturated monomer functions as a crosslinking agent which renders the paint film insoluble. The monounsaturated monomer functions as a reactive diluent, by means of which the viscosity is reduced without a solvent having to be used.

Such two- and three-component systems based on a prepolymer are used both for printing inks and for paint, photoresists or other photocurable compositions. One-component systems based on photocurable prepolymers are frequently also used as binders for printing inks.

Unsaturated polyester resins are in most cases used in two-component systems together with a monounsaturated monomer, preferably with styrene. Specific one-component systems, for example polymaleimides, polychalkones or polyimides, such as are described in German Offenlegungsschriften 2,308,830, are frequently used for photoresists.

The unsaturated compounds can also be used in a mixture with non-photopolymerizable film-forming components. These can be, for example, physically drying polymers or solutions thereof in organic solvents, for example nitrocellulose or cellulose acetobutyrate. However, these can also be chemically or thermally curable resins, such as polyisocyanates, polyepoxides or melamine resins. The additional use of thermally curable resins is of importance for the use in so-called hybrid systems, which are photopolymerized in a first stage and crosslinked by thermal aftertreatment in a second stage.

In addition to the photoinitiator, the photopolymerizable mixtures can contain diverse additives. Examples of these are thermal inhibitors which are intended to prevent premature polymerization, for example hydroquinone or sterically hindered phenols. For example copper compounds, phosphorus compounds, quaternary ammonium compounds or hydroxylamine derivatives can be used for improving the storage stability in the dark. In order to exclude atmospheric oxygen during the polymerization, paraffin or similar waxy substances can be added, which migrate to the surface at the start of the polymerization. Small quantities of UV absorbers, for example those of the benzotriazole, benzophenone or oxanilide type, can be added as light stabilizers. Even better is the addition of light stabilizers which do not absorb UV light, such as sterically hindered amines (HALS).

In certain cases, it can be of advantage to use mixtures of two or more of the photoinitiators according to the invention. Of course, mixtures with known photoinitiators can also be used, for example mixtures with benzophenone, acetophenone derivatives, benzoin ethers or benzil ketals.

To accelerate the photopolymerization, amines can be added, such as triethanolamine, N-methyl-diethanolamine, ethyl p-dimethylaminobenzoate or Michler's ketone. The effect of the amines can be intensified by the addition of aromatic ketones of the benzophenone type.

An acceleration of the photopolymerization can also be effected by an addition of photosensitizers, which shift or broaden the spectral sensitivity. These are especially aromatic carbonyl compounds, for example derivatives of benzophenone, thioxanthone, anthraquinone and 3-acylcoumarin, and also 3-(aroylmethylene)-thiazolines. Further conventional additives—depending on the intended use—are fillers, pigments, dyes, wetting agents or levelling agents.

The invention therefore also relates to photopolymerizable compositions which contain
 a) at least one ethylenically unsaturated photopolymerizable compound and
 b) at least one compound of the formula I as a photoinitiator,
it being possible for the composition in addition to contain also another photoinitiator and/or other additives.

The photopolymerizable compositions contain the photoinitiator (b) advantageously in a quantity from 0.05 to 15% by weight, preferably 0.2 to 5% by weight, relative to the composition.

The photopolymerizable compositions can be used for various purposes, for example as a printing ink, as a white enamel, as a paint, as a paint for exterior coatings, for photographic reproduction processes, for image recording processes or for the production of printing plates, as dental filling compositions, as adhesives, as coatings for optical fibres, for printed circuits or for coating electronic components.

The polymerization is carried out by the known methods of photopolymerization by means of irradiation with sunlight or with light rich in shortwave radiation. Suitable light sources are, for example, mercury medium-pressure, high-pressure and low-pressure radiators, superactinic fluorescent tubes, metal halide lamps or lasers, whose emission maxima are in the range between 250 and 450 nm. In the case of a combination with photosensitizers, longer-wave light or laser beams up to 600 nm can also be used.

The examples which follow explain the invention in more detail. In the same way as in the rest of the description and in the patent claims, data in parts or percent relate to the weight, unless otherwise stated.

EXAMPLE 1

Preparation of bis-(2-phenylpropyl)-(2,6-dimethoxybenzoyl)-phosphine oxide 6.9 ml (0.011 mol, 1.6M) of butyllithium are added dropwise under argon at 0° C. in the course of 10 minutes to a solution of 1.1 g (0.011 mol) of diisopropylamine in 10 ml of absolute tetrahydrofuran (THF). This solution is added dropwise at −20° to −30° C. in the course of about 40 minutes to a solution of 2.2 g (0.011 mol) of 2,6-dimethoxybenzoyl chloride and 2.7 g (0.01 mol) of bis-(2-phenylpropyl)-phosphine in 20 ml of absolute THF.

After stirring at −30° C. for 2 hours, the yellow solution is allowed to warm to room temperature, diluted with 100 ml of toluene and washed once with water and once with saturated bicarbonate solution. The organic phase is dried with magnesium sulfate, filtered and concentrated in a rotary evaporator. The residue is dissolved in 40 ml of acetonitrile, and 1.1 g (0.01 mol) of 30% hydrogen peroxide are added. After stirring for 1 hour at 50° C., the mixture is diluted with toluene, washed with brine and saturated sodium carbonate solution, dried with magnesium sulfate and evaporated in a rotary evaporator. After purification by means of chromatography (solvent: hexane/ethyl acetate 1:1), this gives 3.1 g, i.e. 68.9% of theory, of the abovementioned title compound as a yellow oil.

| Elemental analysis | calc. | C 71.98% | H 6.94% |
|---|---|---|---|
|  | found | C 71.45% | H 7.05% |

EXAMPLE 2

Preparation of bis-(2-phenylpropyl)-(2,4,6-trimethylbenzoyl)-phosphine oxide

The phosphine oxide named above is prepared analogously to the method described in Example 1:

| Elemental analysis | calc. | C 77.75% | H 7.69% |
|---|---|---|---|
|  | found | C 77.24% | H 7.72% |

EXAMPLE 3

Preparation of diphenyl-[2,2-bis-(chloromethyl)-propionyl]-phosphine oxide 3.8 g (0.02 mol) of dichloropivaloyl chloride are introduced into 20 ml of toluene and heated to 80° C. 4.3 g (0.02 mol) of methoxydiphenylphosphine are added dropwise in the course of about 5 minutes to this solution, methyl chloride escaping. After stirring for 1 hour at 80° C., the slightly yellow solution is cooled to room temperature and evaporated in a rotary evaporator. After purification by means of chromatography (solvent: hexane/ethyl acetate 3:1), this gives 1.6 g, i.e. 22.8% of theory, of the abovementioned compound as a yellow resin.

| Elemental analysis | calc. | C 57.48% | H 4.82% | Cl 19.96% |
|---|---|---|---|---|
|  | found | C 57.37% | H 5.16% | Cl 18.84% |

EXAMPLE 4

Preparation of ethoxy-(2,6-dimethoxybenzoyl)-(diethoxymethyl)-phosphine oxide

The preparation is carried out analogously to the method described in Example 3. This gives the compound having a melting point of 81° C.

| Elemental analysis | calc. | C 53.33% | H 6.99% | P 8.60% |
|---|---|---|---|---|
|  | found | C 53.15% | H 6.94% | P 9.24% |

EXAMPLE 5

Preparation of diphenyl-[(1,2,2-trimethyl-3-methoxycarbonyl)-cyclopent-1-yl]-phosphine oxide The preparation is carried out analogously to the method described in Example 3. This gives the compound as an oil in a yield of 28.2% of theory.

| Elemental analysis | calc. | C 69.33% | H 6.83% |
|---|---|---|---|
|  | found | C 68.75% | H 6.87% |

EXAMPLE 6

Preparation of bis(2,6-dimethoxybenzoyl)-benzylphosphine oxide

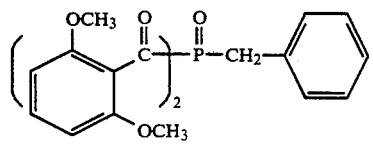

To a solution of 71.1 g (0.354 mol) of 2,6-dimethoxybenzoyl chloride in 300 ml of toluene is added a mixture of 52.6 g (0.161 mol) of benzylphosphine (38% in toluene) and 49.3 ml (0.345 mol) of triethylamine at 100°-110° C. in the course of 30 min. To complete the reaction the mixture is stirred for 6 h at the same temperature. Then the reaction mixture is diluted in toluene and twice washed with water and a diluted solution of bicarbonate. While stirring and cooling 18.2 g (0.161 mol) of 30% hydrogen peroxide are added to the organic phase in the course of 20 min. Then stirring of the reaction mixture is continued for 1 h. After twice washing the reaction mixture with water and a diluted solution of bicarbonate the organic phase is dried with magnesium sulfate, filtered and concentrated in vacuum. The reaction product is crystallized from acetic acid ethylester. 24.8 g (32.9% of theory) of the title compound are obtained.

| Melting point: | 193-194° C. | | |
|---|---|---|---|
| Elemental analysis: | calc. | C 64.10% | H 5.38% |
| | found | C 64.16% | H 5.40% |

EXAMPLE 7

Preparation of bis(2,6-dichlorobenzoyl)-benzylphosphin oxide

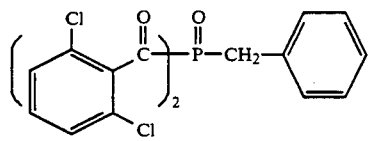

The compound of example 7 is prepared according to the procedure described in example 6, replacing the 2,6-dimethoxybenzoyl chloride by 2,6-dichlorobenzoyl chloride. 23.8 g (40.4% of theory) of the title compound are obtained.

| Melting point: | 149-151° C. | | | |
|---|---|---|---|---|
| Elemental analysis: | calc. | C 51.89% | H 2.70% | Cl 29.17% |
| | found | C 51.82% | H 2.80% | Cl 28.94% |

EXAMPLE 8

Preparation of
9-(2,4,6-Trimethylbenzoyl)-9-phosphabicyclo[4.2.1]nonan-9-oxide (I) and
9-(2,4,6-Trimethylbenzoyl)-9-phosphabicyclo[3.3.1]nonan-9-oxide (II)

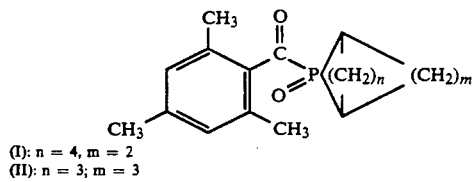

(I): n = 4, m = 2
(II): n = 3; m = 3

To 20.7 g (0.146 mol) of an isomeric mixture of 9H-9-phosphabicyclo[3.3.1]-nonan and 9H-9-phosphabicyclo[4.2.1]-nonan (®Phoban; HOECHST) diluted in 100 ml of absoluted tetrahydrofuran 100 ml (0.16 mol) of butyl lithium (1.6 molar in hexane) are added at a temperature of 20°-30° C. in the course of 30 min. The reaction mixture is then heated to 40° C. and stirred at this temperature for 1 h. This mixture is added at -30° C. in the course of 60 min. to a solution of 29.2 g (0.146 mol) of 2,4,6-trimethylbenzoyl chloride in 150 ml of absoluted tetrahydrofuran. To complete the reaction the mixture is stirred for 3 h. Then the mixture is allowed to warm to room temperature and twice washed with water and saturated bicarbonate solution. The organic phase is dried with magnesium sulfate, filtered and concentrated in vacuum. The residue is dissolved in 200 ml of toluene. While stirring and cooling 16.5 g (0.146 mol) of 30% hydrogen peroxide are added at 20°-30° C. in the course of 20 min. After stirring for 1 h at the same temperature the reaction mixture is twice washed with water and diluted bicarbonate solution, dried with magnesium sulfate, filtrated and concentrated in vacuum. The two isomers are separated by means of chromatography (solvent: hexane/acetic acid ethylester 4:1) and recrystallized out of cyclohexane. This results in 10.0 g (22% of theory) of title compound (I), melting point 82°-83° C. and 6.0 g (13.5% of theory) of title compound (II), melting point 90°-91° C.

| Elemental analysis: | | | |
|---|---|---|---|
| Compound (I) | calc. | C 71.03% | H 8.28% |
| | found | C 70.88% | H 8.49% |
| Compound (II) | calc. | C 71.03% | H 8.28% |
| | found | C 69.99% | H 8.17% |

EXAMPLE 9

Preparation of
9-(2,6-Dimethoxybenzoyl)-9-phosphabicyclo[4.2.1]nonan-9-oxide (I) and
9-(2,6-Dimethoxybenzoyl)-9-phosphabicyclo[3.3.1]nonan-9-oxide (II)

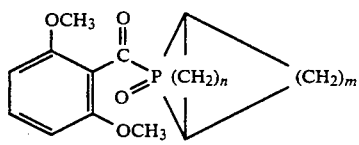

(I): n = 4, m = 2
(II): n = 3; m = 3

The compound of example 9 is prepared according to the procedure described in example 6 replacing the 2,4,6-trimethylbenzoyl chloride by 2,6-dimethoxybenzoyl chloride. The separation of the two isomers is carried out by means of chromatography as described in example 8.

| Melting points: | | | |
|---|---|---|---|
| compound (I) | 127-128° C. | | |
| compound (II) | 163-164° C. | | |
| Elemental analysis: | | | |
| compound (I) | calc. | C 63.35% | H 7.19% |
| | found | C 63.22% | H 7.11% |
| compound (II) | calc. | C 63.35% | H 7.19% |
| | found | C 63.14% | H 7.13% |

EXAMPLE 10

Preparation of
9-Pivaloyl-9-phosphabicyclo[4.2.1]nonan-9-oxide (I)
and 9-Pivaloyl-9-phosphabicyclo[3.3.1]nonan-9-oxide (II)

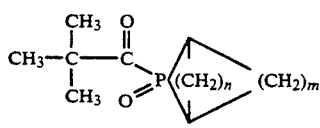

To a solution of 12.1 g (0.10 mol) pivaloylchloride in 100 ml toluene are introduced 26,7 g (0,11 mol) of an isomeric mixture of 9-trimethylsilyloxy-9-phosphabicyclo[4.2.1]nonan and 9-trimethylsilyloxy-9-phosphabicyclo[3.3.1]nonan in an inert gas atmosphere (nitrogen) at 0.5° C. in the course of 20 min. After stirring for 30 min at 0°–5° C. the yellowish solution is allowed to warm to ambient temperature and concentrated at a rotation evaporator. After purificaton by means of chromatography (eluent: acetic acid ester) 4.0 g (16.5% of theory) of (I) as waxy product and 7.3 g (30.2% of theory) of (II) as white powder with a melting point of 77°–78° C. are obtained.

EXAMPLE 11

Preparation of
Benzyl-butyl-(2,6-dimethoxybenzoyl)phosphin oxide

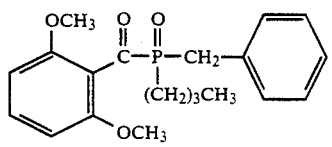

To a solution of 13.2 g (0.067 mol) of benzyl-butyl-phosphin oxide and 12.7 ml (0.101 mol) of trimethylchlorosilane in 100 ml of tetrahydrofuran are added 18.7 ml (0.134 mol) of triethylamine under a nitrogen atmosphere at 0°–5° C. in the course of 15 minutes. After 2 hours of stirring at 0°–5° C., 13.5 g (0.067 mol) of 2,6-dimethoxybenzoyl chloride, diluted in 50 ml of tetrahydrofuran, are added during the course of 20 min. the stirring at 0°–5° C. is continued for 2 h, then the solution is allowed to warm to room temperature and filtered over silicea gel. The solution is concentrated in vacuo and the residue recrystallized from a hexan/acetic acid ester mixture. 3.8 g (15.8% of theory) of the title compound with a melting point of 56°–57° C. are obtained.

| Elemental analysis: | calc. | C 66.66% | H 6.99% |
|---|---|---|---|
| | found | C 66.58% | H 7.24% |

EXAMPLE 12

Preparation of
Benzyl-butyl-(2,4,6-trimethylbenzoyl)phosphin oxide

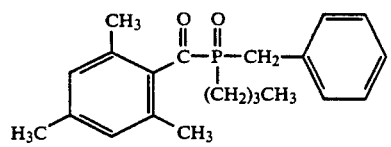

Following the preparation method of example 11, but replacing the 2,6-dimethoxybenzoyl chloride by 2,4,6-trimethylbenzoyl chloride, benzyl-butyl-(2,4,6-trimethylbenzoyl)phosphin oxide is obtained as yellow, slightly viscous oil.

| Elemental analysis: | calc. | C 73.66% | H 7.95% |
|---|---|---|---|
| | found | C 73.42% | H 8.05% |

EXAMPLE 13

Initiator reactivity in a white enamel topcoat

A white enamel is prepared from
30 parts of ®Ebecryl 608 (epoxyacrylate from UCB, Belgium)
15 parts of trimethylolpropane trisacrylate
5 parts of N-vinylpyrrolidone
50 parts of titanium dioxide (rutile).

Two per cent by weight of the photoinitiator to be tested are incorporated into the white enamel and the formulation is applied in a layer thickness of 100 μm to aluminium sheets which have been primed with a white coil coat. The samples are fully cured under an Hg medium-pressure lamp (Hanovia, 80 W/cm). Full curing has taken place when the underside of a paint film which has been separated off is dry. To measure the reactivity, the number of passes under the lamp at a defined belt speed is determined. In addition, the reactivity is measured after a pre-exposure of one minute under 5 40 W lamps (Philips TL03). The pendulum hardness (according to König, DIN53157), the yellowing (Yellowness Index, ASTM D 1925-70) and the gloss at 20° and 60° (multi-gloss apparatus, ASTM D 523) are measured directly after curing and after additional irradiation for 15 minutes of 16 hours (gloss) under 5 40 W lamps (Philips TL03). The results are reproduced in Tables 1 and 2.

TABLE 1

| | | White enamel topcoat without pre-exposure | | | | | |
|---|---|---|---|---|---|---|---|
| | | Pendulum hardness [sec] | | Yellowness Index | | Gloss (20/60°) | |
| Compound according to Example | Wiping resistance* | immediately | after 15 minutes | immediately | after 15 minutes | immediately | after 16 hours |
| 2 | 6 | 43 | 70 | 1.2 | 0.8 | 78/90 | 77/90 |
| 1 | 7 | 36 | 90 | 1.1 | 0.8 | 81/91 | 79/92 |

*as the number of passes at 20 m/minute

TABLE 2

| Compound according to Example | Wiping resistance* | White enamel topcoat with pre-exposure | | | | | |
|---|---|---|---|---|---|---|---|
| | | Pendulum hardness [sec] | | Yellowness Index | | Gloss (20/60°) | |
| | | immediately | after 15 minutes | immediately | after 15 minutes | immediately | after 16 hours |
| 1 | 7 | 35 | 76 | 1.6 | 1.2 | 81/91 | 80/91 |
| 2 | 8 | 38 | 56 | 1.8 | 1.4 | 59/89 | 58/89 |

*as the number of passes at 20 m/minute

Example 14

Initiator reactivity in a clearcoat

A clearcoat is prepared from
99.5 parts of ®Roskydal UV 502 A (solution of an unsaturated polyester in styrene, from BAYER, Federal Republic of Germany)
0.5 part of ®Byk 300 (additive).
Two per cent by weight of the photoiniator to be tested are mixed in, and the formulation is applied in a coating thickness of 100 μm to chipboard coated with a white synthetic resin.

The samples are irradiated in a PPG irradiation apparatus with Hg medium-pressure lamps (2×80 W/cm). The belt speed in m/minute is then determined which is necessary to obtain a wiping-resistant paint surface. The hardness is determined by measuring the König pendulum hardness (DIN 53157) and the yellowing is measured as the yellowness index (ASTM D 1925-70).

The results are reproduced in Table 3.

TABLE 3

| Compound according to Example | Wiping resistance [number of passes at 20 m/min] | Pendulum hardness [seconds] | Yellowness Index |
|---|---|---|---|
| 3 | 5 | 82 | 6.6 |
| 5 | 6 | 83 | 6.7 |

What is claimed is:

1. A compound of the formula I

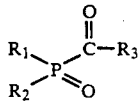

in which $R_1$ is $C_1$–$C_{18}$alkyl, $C_2$–$C_{18}$alkenyl, $C_1$–$C_8$alkyl which is monosubstituted or polysubstituted by phenyl, ($C_1$–$C_{12}$alkyl)-phenyl, halogenophenyl, ($C_1$–$C_{12}$alkoxy)-phenyl, cyano, $C_2$–$C_5$alkoxycarbonyl, $C_1$–$C_{12}$alkoxy or/and halogen, $C_5$–$C_8$cycloalkyl, $C_6$–$C_{12}$aryl, which is unsubstituted or mono- or poly-substituted by halogen, $C_1$–$C_{12}$alkyl or/and $C_1$–$C_{12}$alkoxy, a 5-membered or 6-membered heterocyclic monovalent radical which contains one or more O, S or/and N atoms and which may contain a fused benzo radical or/and which is unsubstituted or substituted by $C_1$–$C_4$alkyl, $C_1$–$C_4$alkoxy or/and halogen, or is a radical of the formula

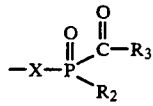

in which X is phenylene, xylylene, cyclohexylene or $C_1$–$C_6$alkylene which may be unsubstituted or mono-substituted or polysubstituted by halogen, $C_1$–$C_4$alkyl, $C_1$–$C_4$alkoxy or phenyl, $R_2$ is $C_1$–$C_{18}$alkyl, $C_2$–$C_{18}$alkenyl, $C_1$–$C_8$alkyl which is monosubstituted or polysubstituted by phenyl, ($C_1$–$C_{12}$alkyl)-phenyl, halogenophenyl, ($C_1$–$C_{12}$alkoxy)-phenyl, cyano, $C_2$–$C_5$alkoxycarbonyl, $C_1$–$C_{12}$alkoxy or/and halogen, $C_5$–$C_8$cycloalkyl, $C_6$–$C_{12}$aryl which is unsubstituted or mono- or polysubstituted by halogen, $C_1$–$C_{12}$alkyl or/and $C_1$–$C_{12}$alkoxy, a 5-membered or 6-membered heterocyclic monovalent radical which contains one or more O, S or N atoms and which may contain a fused benzo radical or/and is unsubstituted or substituted by $C_1$–$C_4$alkyl, $C_1$–$C_4$alkoxy or/and halogen, or is a radical —CO—$R_3$ or —O$R_4$, or $R_1$ and $R_2$ together with the phosphorus atom form a bicyclic phosphabicyclohexane or phosphabicyclononane ring, $R_3$ is $C_1$–$C_{18}$alkyl, $C_2$–$C_6$alkenyl, phenylvinyl, $C_1$–$C_8$alkyl which is mono- or poly-substituted by phenyl, $C_2$–$C_5$alkoxycarbonyl, halogen, $C_1$–$C_{12}$alkoxy, phenoxy, $C_1$–$C_{12}$alkylthio or/and phenylthio, $C_6$–$C_{12}$aryl which is unsubstituted or mono- or poly-substituted by $C_1$–$C_{12}$alkyl, $C_1$–$C_{12}$alkoxy, $C_1$–$C_{12}$alkoxyalkyl, $C_1$–$C_4$alkylthio or/and halogen, or a monovalent 5-membered or 6-membered heterocyclic radical containing one or more O, S or N atoms, which radical can be mono- or poly-substituted halogen, $C_1$–$C_4$alkyl or $C_1$–$C_4$alkoxy, and $R_4$ is $C_1$–$C_{18}$alkyl, phenyl-$C_1$–$C_4$alkyl, $C_5$–$C_8$cycloalkyl or $C_6$–$C_{10}$aryl, with the proviso that at least one of the radicals $R_1$, $R_2$ and $R_3$ is a substituted alkyl radical or that $R_1$ and $R_2$ together with the phosphorus atom form a bicyclic ring.

2. A compound according to claim 1 of the formula I, in which $R_1$ is $C_1$–$C_{12}$alkyl, $C_1$–$C_4$alkyl which is mono- to tri-substituted by phenyl, ($C_1$–$C_4$alkyl)-phenyl, chlorophenyl, ($C_1$–$C_4$alkoxy)-phenyl or/and $C_1$–$C_4$alkoxy, cyclohexyl, $C_6$–$C_{10}$aryl which is unsubstituted or mono- to tri-substituted by chlorine, $C_1$–$C_{12}$alkyl or/and $C_1$–$C_4$alkoxy, or is a 5-membered or 6-membered heterocyclic monovalent radical which contains one or more O, S or N atoms, $R_2$ is as defined for $R_1$ or a radical —CO—$R_3$ or —O$R_4$, or $R_1$ and $R_2$ together with the P atom form a bicyclic radical having, $R_3$ is $C_1$–$C_8$alkyl, $C_1$–$C_6$alkyl which is mono- or di-substituted by phenyl, $C_1$–$C_4$alkoxy, $C_2$–$C_5$alkoxycarbonyl or/and chlorine, or $C_6$–$C_{10}$aryl which is unsubstituted or mono- to tri-substituted by $C_1$–$C_{12}$alkyl, $C_1$–$C_4$alkoxy or/and chlorine, and $R_4$ is $C_1$–$C_8$alkyl, cyclohexyl, benzyl or phenyl.

3. A compound according to claim 1 of the formula I, in which $R_1$ is $C_1$–$C_8$alkyl, $C_1$–$C_4$alkyl which is mono- or di-substituted by phenyl ($C_1$–$C_4$alkyl)-phenyl or $C_1$–$C_1$alkoxy, cyclohexyl or phenyl which is unsubstituted or mono- to tri-substituted by $C_1$–$C_4$alkyl or $C_1$–$C_4$alkoxy, $R_2$ is as defined for $R_1$ or is a radical —CO—$R_3$ or —O$R_4$, or $R_1$ and $R_2$ or $R_1$ and $R_4$ together with the P atom form a monocyclic or bicyclic ring, $R_3$ is $C_1$–$C_6$alkyl which is unsubstituted or substituted by phenyl, chlorine or/and $C_1$–$C_4$alkoxy, or phenyl which is unsubstituted or mono- to tri-substituted by $C_1$–$C_4$alkyl, $C_1$–$C_4$alkoxy or/and chlorine, and $R_4$ is $C_1$–$C_4$alkyl, cyclohexyl or phenyl.

4. A compound according to claim 1 of the formula I, in which $R_1$ is a substituted alkyl radical as defined in claim 1.

5. A compound according to claim 4, in which $R_1$ is $C_1$–$C_4$alkyl which is substituted by phenyl, ($C_1$–$C_4$alkyl)-phenyl, chlorophenyl, $C_1$–$C_4$alkoxy or cyano.

6. A compound according to claim 1 of the formula I, in which $R_1$ is benzyl.

7. A compound according to claim 1 of the formula I, in which $R_2$ is $C_1$–$C_4$alkyl which is unsubstituted or substituted by phenyl, ($C_1$–$C_4$alkyl)-phenyl, chlorophenyl, $C_1$–$C_4$alkoxy or cyano, or is phenyl or cycloalkyl.

8. A compound according to claim 1 of the formula I, in which $R_3$ is phenyl which is substituted by $C_1$–$C_4$alkyl, $C_1$–$C_4$alkoxy or chlorine.

9. A compound according to claim 1 of the formula I, in which $R_3$ is $C_1$–$C_8$alkyl which is mono- to tri-substituted by phenyl, $C_2$–$C_5$alkoxycarbonyl, halogen or-/and $C_1$–$C_{12}$alkyl.

10. A compound according to claim 1 of the formula II or III

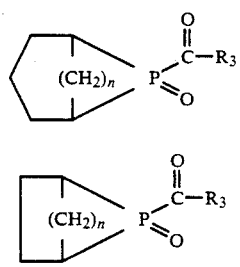

in which n is 1–8 and $R_3$ is as defined in claim 1.

11. A compound according to claim 10 of the formula II or III, in which n is 1–8 and $R_3$ is phenyl-substituted $C_1$–$C_4$alkyl, $C_6$–$C_{10}$aryl or phenyl which is mono- to tri-substituted by $C_1$–$C_{12}$alkyl, $C_1$–$C_4$alkoxy or chlorine.

12. A compound according to claim 1 of the formula I, in which $R_2$ is a radical —CO-$R_3$.

13. A compound according to claim 1 of the formula I, in which $R_1$ is $C_1$–$C_4$alkyl which is unsubstituted or substituted by phenyl, $C_1$–$C_4$alkoxy or chlorine, phenyl or ($C_1$–$C_4$alkyl)-phenyl, $R_2$ is as defined for $R_1$ or is —O—($C_1$–$C_4$alkyl) and $R_3$ is phenyl which is unsubstituted or substituted by $C_1$–$C_4$alkyl, $C_1$–$C_4$alkoxy or-/and chlorine, or $R_3$ is $C_1$–$C_4$alkyl which is unsubstituted or substituted by chlorine, $C_1$–$C_4$alkoxy or phenyl.

14. A compound according to claim 1 of the formula I, in which $R_1$ is $C_1$–$C_4$alkyl substituted by phenyl or $C_1$–$C_4$alkoxy, or phenyl, $R_2$ is as defined for $R_1$ or is —O—($C_1$–$C_4$alkyl) and $R_3$ is phenyl substituted by $C_1$–$C_4$alkyl or $C_1$–$C_4$alkoxy, or $R_3$ is $C_1$–$C_4$alkyl substituted by chlorine.

15. A photopolymerizable composition, containing
 a) at least one ethylenically unsaturated photopolymerizable compound and
 b) at least one compound of the formula I as defined in claim 1 as a photoinitiator.

16. A composition according to claim 15, which contains, in addition to the photoinitiator (b) also another photoinitiator and/or other additives.

17. A composition according to claim 15, containing 0.05 to 15% by weight of component (b), relative to the composition.

18. A composition according to claim 15, containing 0.2 to 5% by weight of component (b), relative to the composition.

19. A composition according to claim 15, which contains at least one further photoinitiator.

20. A process for photopolymerizing non-volatile monomeric, oligomeric or polymeric compounds having at least one ethylenically unsaturated double bond, which comprises adding a compound of the formula I according to claim 1 to the said compounds alone or in combination with another photoinitiator and/or other additives and irradiating with light in the range from 200 to 600 nm.

* * * * *